(12) United States Patent
Podany (10) Patent No.: US 11,071,579 B2
(45) Date of Patent: Jul. 27, 2021

(54) BIPOLAR CUTTING AND HEMOSTASIS BLADE SYSTEM

(71) Applicant: Medtronic Advanced Energy LLC, Minneapolis, MN (US)

(72) Inventor: Vini Podany, New Fairfield, CT (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 770 days.

(21) Appl. No.: 15/856,887

(22) Filed: Dec. 28, 2017

(65) Prior Publication Data

US 2018/0206903 A1    Jul. 26, 2018

Related U.S. Application Data

(60) Provisional application No. 62/448,673, filed on Jan. 20, 2017.

(51) Int. Cl.
| | |
|---|---|
| *A61B 18/14* | (2006.01) |
| *A61B 18/08* | (2006.01) |
| A61B 18/12 | (2006.01) |
| A61B 18/00 | (2006.01) |
| A61B 18/18 | (2006.01) |
| A61B 17/29 | (2006.01) |

(52) U.S. Cl.
CPC ........ *A61B 18/1442* (2013.01); *A61B 18/082* (2013.01); *A61B 18/1402* (2013.01); *A61B 18/148* (2013.01); *A61B 17/2909* (2013.01); *A61B 2018/00601* (2013.01); *A61B 2018/126* (2013.01); *A61B 2018/1412* (2013.01); *A61B 2018/1425* (2013.01); *A61B 2018/1465* (2013.01); *A61B 2018/1475* (2013.01); *A61B 2018/1861* (2013.01); *A61B 2218/002* (2013.01); *A61B 2218/007* (2013.01)

(58) Field of Classification Search
CPC .............. A61B 18/1442; A61B 18/082; A61B 18/1402; A61B 18/148
See application file for complete search history.

(56) References Cited

U.S. PATENT DOCUMENTS

| | | |
|---|---|---|
| 5,944,718 A | 8/1999 | Austin et al. |
| 8,080,009 B2 | 12/2011 | Lee et al. |
| 2004/0193152 A1* | 9/2004 | Sutton ................ A61B 18/1477 606/48 |
| 2004/0260280 A1* | 12/2004 | Sartor ................ A61B 18/1482 606/37 |
| 2005/0043728 A1 | 2/2005 | Ciarrocca |

(Continued)

*Primary Examiner* — Michael F Peffley
*Assistant Examiner* — Bo Ouyang
(74) *Attorney, Agent, or Firm* — Christopher & Weisberg, P.A.

(57) ABSTRACT

An electrosurgical medical device includes an elongate shaft defining a proximal end, a distal end, and a lumen there through. A fluid conduit is disposed within the lumen. A first electrode is at least partially disposed within the lumen and extends distally from the distal end of the shaft, the first electrode is sized and configured to cut tissue with radiofrequency energy. A second electrode is arranged in a bipolar configuration with the first electrode, the second electrode is coupled to ground and configured to receive radiofrequency energy from the first electrode. The second electrode is defined by at least a portion the shaft and extending a distance away from the distal end of the shaft.

18 Claims, 5 Drawing Sheets

(56) References Cited

U.S. PATENT DOCUMENTS

| | | | |
|---|---|---|---|
| 2006/0167449 A1* | 7/2006 | Mulier | A61B 18/14 606/41 |
| 2007/0213708 A1 | 9/2007 | Dumbauld et al. | |
| 2011/0178515 A1 | 7/2011 | Bloom et al. | |
| 2013/0053792 A1* | 2/2013 | Fischell | A61M 25/0108 604/275 |
| 2016/0120589 A1 | 5/2016 | Smith et al. | |
| 2016/0242661 A1* | 8/2016 | Fischell | A61B 5/6852 |

* cited by examiner

BIPOLAR CUTTING AND HEMOSTASIS BLADE SYSTEM

CROSS-REFERENCE TO RELATED APPLICATION

This application is related to and claims priority to U.S. Provisional Patent Application Ser. No. 62/448,673, filed Jan. 20, 2017, entitled BIPOLAR CUTTING AND HEMOSTASIS BLADE SYSTEM, the entirety of which is incorporated herein by reference.

STATEMENT REGARDING FEDERALLY SPONSORED RESEARCH OR DEVELOPMENT n/a

TECHNICAL FIELD

This disclosure relates to electrosurgical devices, and in particular, a bipolar radiofrequency device configured to cut tissue.

BACKGROUND

Monopolar electrosurgery typically includes a hand piece having an active electrode which delivers radiofrequency ("RF") energy to the target tissue region, and a return or ground electrode which operates as a pole for the flow of energy from the active electrode. Typically, the return electrode is a pad positioned on the patient's body, and if used or positioned improperly, may result in patient burns. This may occur in part because the energy pathway between the active electrode and the return electrode may not be well defined pathway and thus current may flow to unwanted tissue areas resulting in patient burns. As a result of this drawback, safety concerns exist when using monopolar RF devices to treat nerves around the spine or in brain owing the increased likelihood of collateral damage.

Bipolar electrosurgery typically includes a hand piece having an active electrode and a return electrode on the hand piece itself such that RF energy may flow back-and-forth between the two electrodes. However, current bipolar devices are offered for general surgical procedures for large area tissues such as to treat joints or to coagulate large areas of tissue during surgery. Thus, current bipolar devices are not configured to cut small tissues, such as nerves, or to be used generally for microsurgery.

SUMMARY

Some embodiments advantageously provide a system and medical device for performing electrosurgical procedures using bipolar radiofrequency energy. The electrosurgical medical device includes an elongate shaft defining a proximal end, a distal end, and a lumen there through. A fluid conduit is disposed within the lumen. A first electrode is at least partially disposed within the lumen and extends distally from the distal end of the shaft, the first electrode is sized and configured to cut tissue with radiofrequency energy. A second electrode is arranged in a bipolar configuration with the first electrode, the second electrode is coupled to ground and configured to receive radiofrequency energy from the first electrode. The second electrode is defined by at least a portion the shaft and extending a distance away from the distal end of the shaft.

In another aspect of this embodiment, the second electrode is curvilinear in shape and extends away from the first electrode.

In another aspect of this embodiment, the first electrode defines the fluid conduit.

In another aspect of this embodiment, the first electrode defines a sharp distal end.

In another aspect of this embodiment, the second electrode is atraumatic and flexible.

In another aspect of this embodiment, the surface area of the second electrode is larger than the surface area of the first electrode.

In another aspect of this embodiment, the first electrode is at least substantially entirely coated with an insulating material.

In another aspect of this embodiment, the first electrode is a hypotube with a sharp distal end.

In another aspect of this embodiment, the second electrode is biased in a position away from the shaft.

In another embodiment, the electrosurgical medical device includes an elongate shaft defining a proximal end, a distal end, and a lumen there through. A fluid conduit is disposed within the lumen. A first electrode is at least partially disposed within the lumen and extending distally from the distal end of fluid conduit. The first electrode is sized and configured to cut tissue with radiofrequency energy. A second electrode is arranged in a bipolar configuration with the first electrode. The second electrode is coupled to ground and configured to receive radiofrequency energy from the first electrode. The second electrode is defined by at least a portion the shaft and extending a distance away from the distal end of the shaft. An alignment element is disposed within the lumen of the shaft, the alignment element is configured to maintain the position of the first electrode within the shaft.

In another aspect of this embodiment, the alignment element defines a lumen therein, and wherein the fluid conduit is received within the lumen of the alignment element.

In another aspect of this embodiment, the fluid conduit is in fluid communication with a vacuum source and configured to suction smoke.

In another aspect of this embodiment, the fluid conduit is in fluid communication with a fluid source and configured to provide irrigation.

In another aspect of this embodiment, the alignment element includes a plurality of lumens configured to transport fluid to and from the proximal end and the distal end of the elongate shaft.

In another aspect of this embodiment, the first electrode and the second electrode are configured to coagulate tissue with saline dispersed from the fluid conduit.

In another aspect of this embodiment, the second electrode is curvilinear in shape and extends away from the first electrode.

In another aspect of this embodiment, the first electrode defines a sharp distal end.

In another aspect of this embodiment, the second electrode is atraumatic and flexible.

In another aspect of this embodiment, the surface area of the second electrode is larger than the surface area of the first electrode.

In another embodiment, the electrosurgical medical device includes an elongate shaft defining a proximal end, a distal end, and a lumen there through. A fluid conduit is disposed within the lumen. A first electrode is at least partially disposed within the fluid conduit and extends distally from the distal end of fluid conduit. The first electrode is sized and configured to cut tissue with radiofrequency energy. The first electrode defines a tubular portion sized to be received within the fluid conduit. A second electrode is arranged in a bipolar configuration with the first electrode. The second electrode is coupled to ground and configured to receive radiofrequency energy from the first electrode. The second electrode is defined by at least a portion the shaft and extending a distance away from the distal end of the shaft. A surface area of the second electrode is larger than a surface area of the first electrode, the second electrode defines a curvilinear shape and being flexible. An alignment element is disposed within the lumen of the shaft, the alignment element configured to maintain the position of the first electrode within the shaft.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

As used herein, relational terms, such as "first" and "second," "top" and "bottom," and the like, may be used solely to distinguish one entity or element from another entity or element without necessarily requiring or implying any physical or logical relationship or order between such entities or elements.

Figure 1:
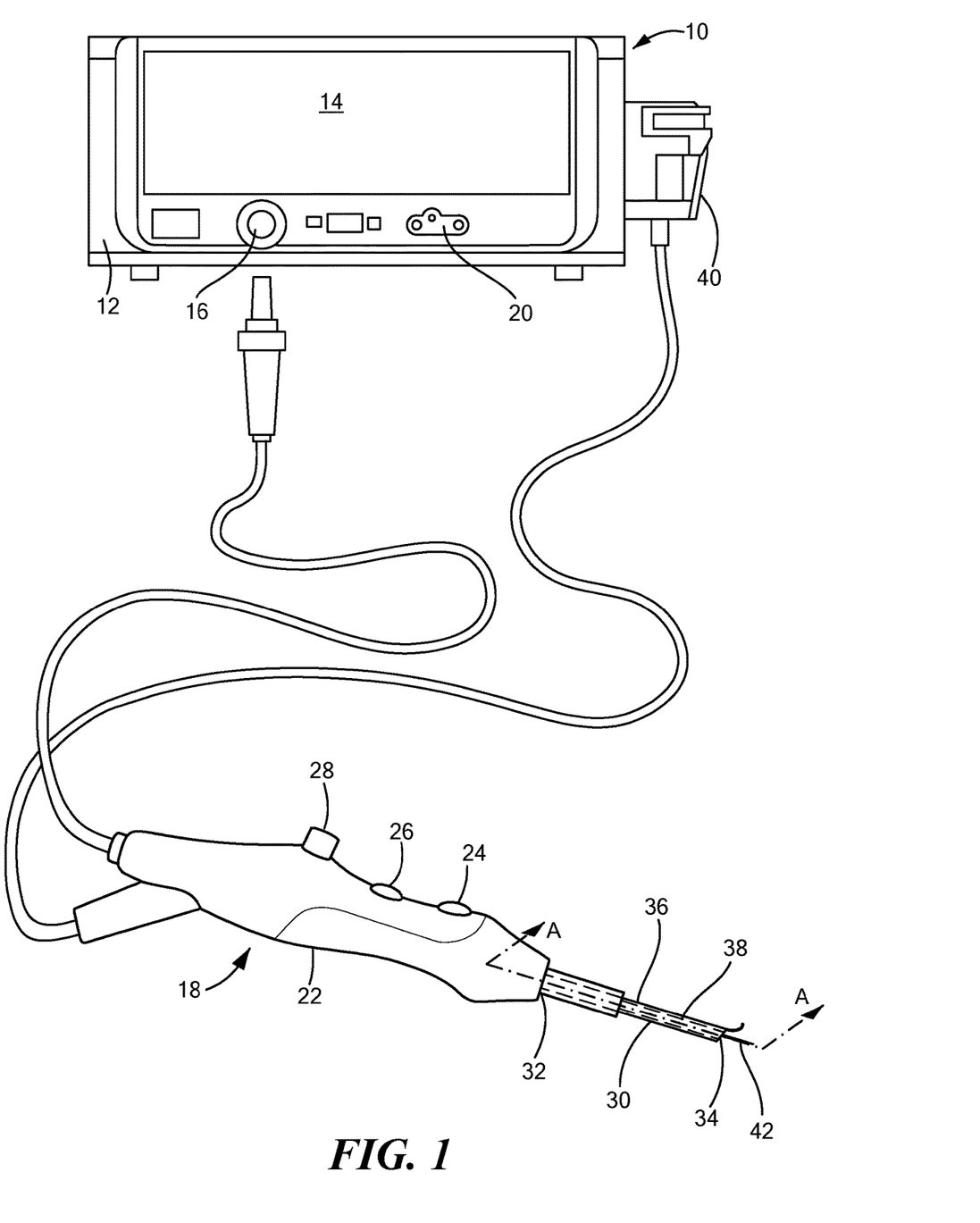
FIG. 1 is a system view of an electrosurgical unit and electrosurgical hand piece constructed in accordance with the principles of the present application.

Referring now to the drawings in which like reference designators refer to like elements, there is shown in FIG. 1 and exemplary electrosurgical unit ("ESU") constructed in accordance with the principles of the present application and designated generally as "10." The ESU 10 may include a radiofrequency generator 12 configured to house and electrically couple the components and circuits of the ESU 10 and a touch actuated display 14 configured to receive energy requests from one or more electrosurgical hand pieces that electrically couple to the radiofrequency generator 12, display treatment progress and measurements, for example, impedance, power, etc. and initiate and/or terminate the supply of radiofrequency energy and fluid with one or more electrosurgical hand pieces that may be electrically coupled to the ESU 10. In an exemplary configuration, the ESU 10 includes a first receptacle 16, which may be a 7-pin connector configured to receive and electrically couple with an electrosurgical hand piece 18 configured to deliver at least one of monopolar radiofrequency energy or a combination of bipolar radiofrequency energy and monopolar radiofrequency energy. The ESU 10 may further include a second receptacle 20, for example, a 3-pin receptacle, configured to receive and electrically couple with a second electrosurgical hand piece (not shown) configured to deliver bipolar radiofrequency energy to tissue. Additional details about an exemplary ESU 10 of the present application may found in U.S. patent application Ser. No. 14/927,999, filed Oct. 30, 2015, entitled RF OUTPUT STAGE SWITCHING MECHANISM, the entirety of which is incorporated herein by reference. In other configurations, the ESU 10 may include a single receptacle configured to deliver one or both of monopolar and bipolar radiofrequency energy and the electrosurgical hand piece may include 7-pin or 3-pin connector to connect with either first receptacle 16 or the second receptacle 20.

Continuing to refer to FIG. 1, the electrosurgical hand piece 18 may include an handle 22 which couples to the first receptacle 16 or second receptacle 20, and includes a first actuator 24 configured to initiate operation of the hand piece 18 in CUT mode, a second actuator 26 configured to initiate operation of the hand piece 18 in COAG mode, and a third actuator 28 configured to initiate operation of the hand piece 18 in TRANS mode. Although three actuators are shown which initiate various functions of the hand piece 18, it is contemplated that only the first actuator 24 may be included, or the first actuator 24 and the second actuator 26 may only be included. As described herein CUT mode operates the hand piece 18 to dissect and/or resect tissue; COAG mode operates the hand piece 18 to coagulate tissue for hemostasis; and TRANS mode operates the hand piece 18 to coagulate tissue while releasing a fluid.

In one configuration, extending distally from the handle 22 may be an elongate shaft 30 defining a proximal end 32, a distal end 34, and a lumen 36 there between. The proximal end 32 of the shaft 30 may be coupled to the distal end of the handle 22. In an exemplary configuration, a first conductor 37 (shown in FIG. 2), which is coupled to ground may extend through the handle 22 and connect to the shaft 30 or extend through the lumen 36 and coupled to the interior surface of the shaft 30. Alternatively, the shaft 30 may be composed of an electrically conductive material, such as stainless steel, and may function as the first conductor 37 to function, in part, as a ground electrode, discussed in more detail below. In one configuration the shaft 30 may be malleable such that it may be manipulated from a first configuration into a second configuration and optionally may be extendable and retractable by pulling or pushing on a finger grip (not shown). In an exemplary configuration, the shaft 30 may be covered with an insulating material such as heat shrink such that the interior of the shaft 30 may be conductive but the exterior of the shaft 30 may be insulated. In one configuration, a fluid conduit 38 may be disposed within the lumen 36 of shaft 30 spanning from the proximal end 32 to the distal end 34. The fluid conduit 38 may be configured to transport fluid, such as saline from the ESU 10 having an integrated fluid source 40 or a separate fluid source 40 to the distal end 34 of the shaft 30. In an exemplary configuration, the fluid conduit 38 may be insulated from the shaft 30 with an insulator 35, such that fluid transported within the fluid conduit 38 is not energized before it exits the distal end 34 of the shaft 30. In another configuration, the fluid conduit 38 is in electrical communication with the shaft 30 such that fluid exiting the distal end 34 of the shaft 30 is energized. In one configuration, the fluid conduit 38 is coaxial—with the lumen 36 of the shaft 30. In another configuration, the fluid conduit 38 is eccentric with respect to the major longitudinal axis defined by the shaft 30.

Figure 2:
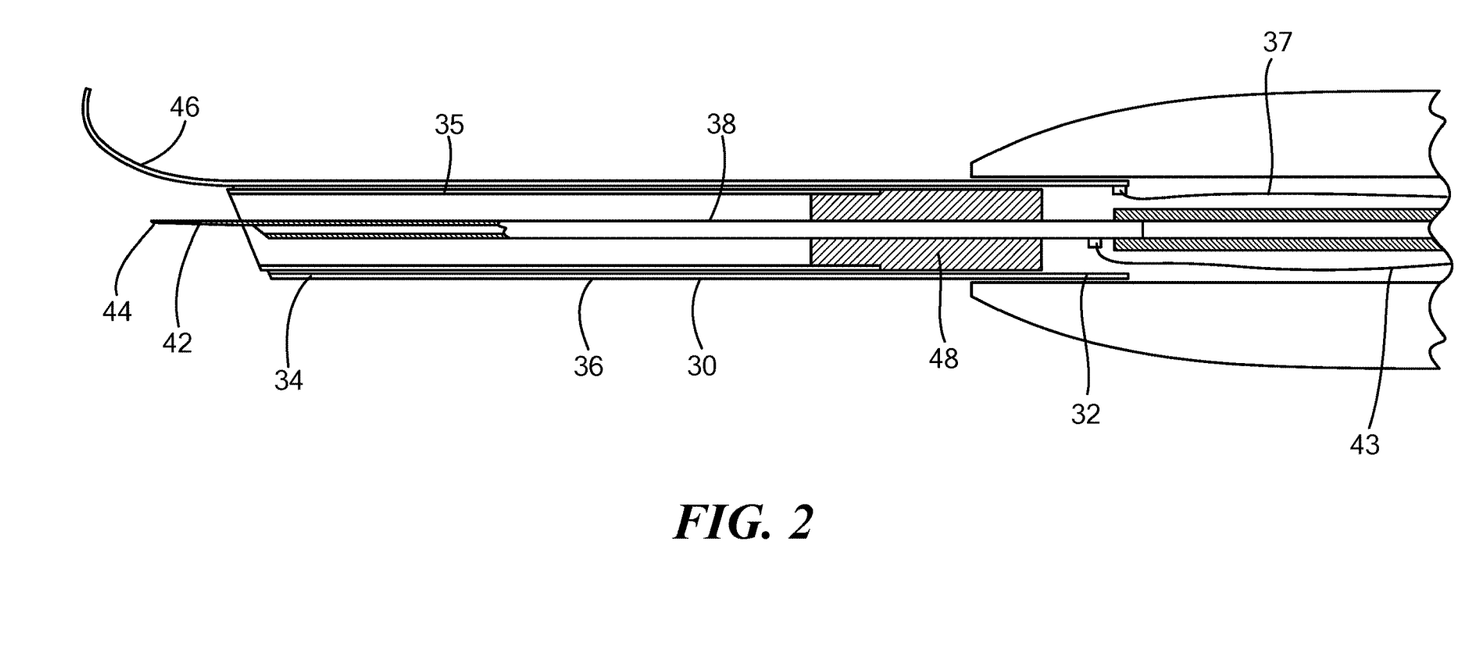
FIG. 2 is a cross-sectional view along Section A-A shown in FIG. 1.

Referring now to FIG. 2, an active electrode 42 may be disposed within the lumen 36 of the shaft 30. The active electrode 42 may be coupled to the distal end of the handle 22 and may further be electrically coupled to the ESU 10. In one configuration, a second conductor 43 may extend through the handle 22 and attached directly to the proximal portion of the active electrode 42 to provide radiofrequency energy to the active electrode. In other configurations, the second conductor 43 may couple to the activate electrode 42 proximate the distal end of the shaft 30. The active electrode 42 may be composed of the electrically conductive material, for example, stainless steel or other metallic alloys, and define a tubular shape or may be solid. In one configuration, the active electrode 42 is a hypotube extending through and co-axial with the shaft 30. The fluid conduit 38 may be concentric about the active electrode 42 such that fluid flows between the outer diameter of the active electrode 42 and in the inner diameter of the fluid conduit 38 or fluid flows within the fluid conduit 38 and through a tubular portion of the active electrode 42. In other configurations, the fluid conduit 38 is not a separate component but is integral with the active electrode 42. For example, the active electrode 42 may define a lumen within which is in fluid communication with the fluid source 40, and during operation of the hand piece 18, fluid is transported from the fluid source 40 through the lumen of the active electrode 42 toward the distal end 34 of the shaft 30.

Figure 3:
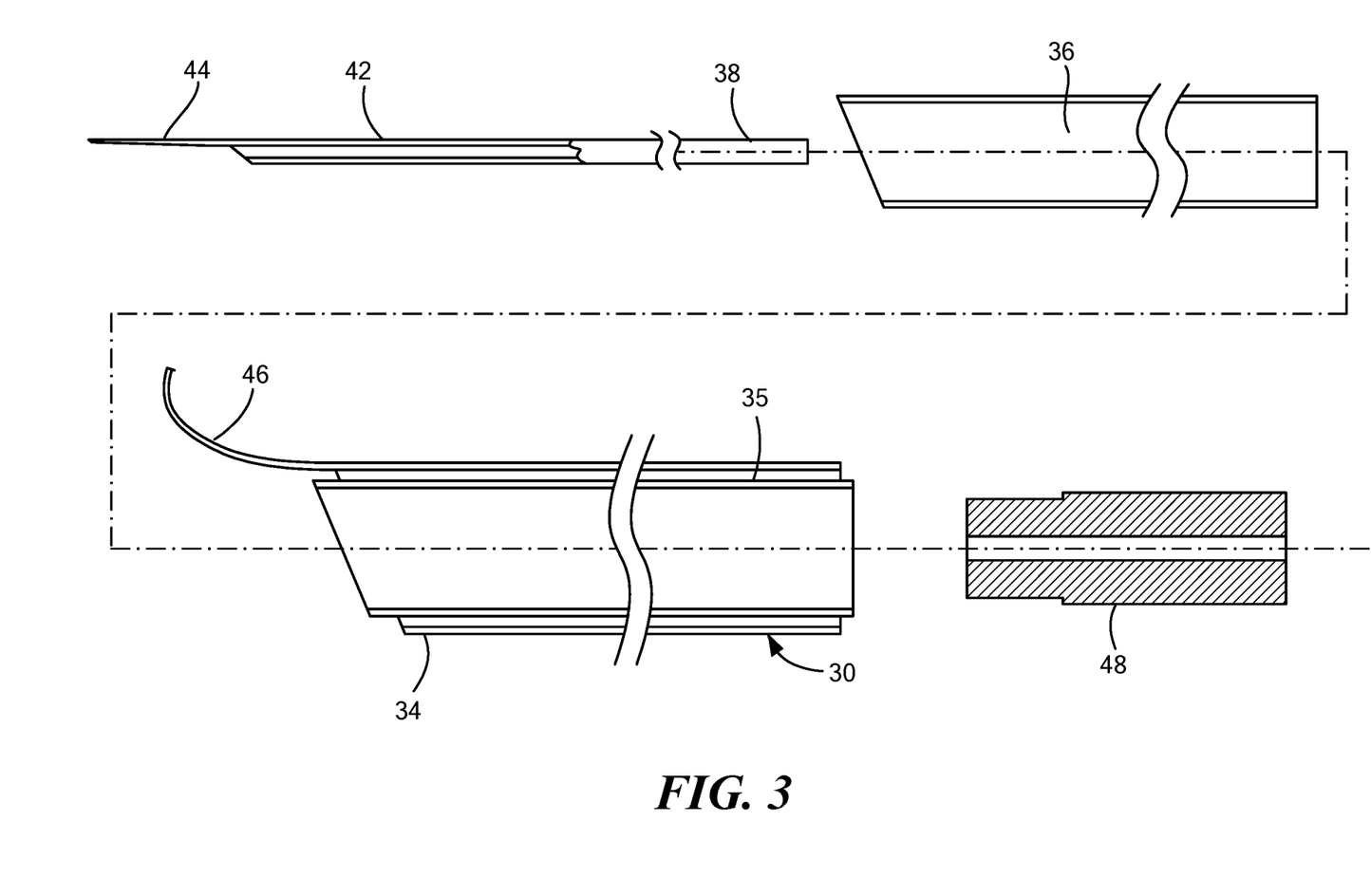
FIG. 3 is an exploded view of the distal portion of the hand piece shown in FIG. 2.
Figure 4:
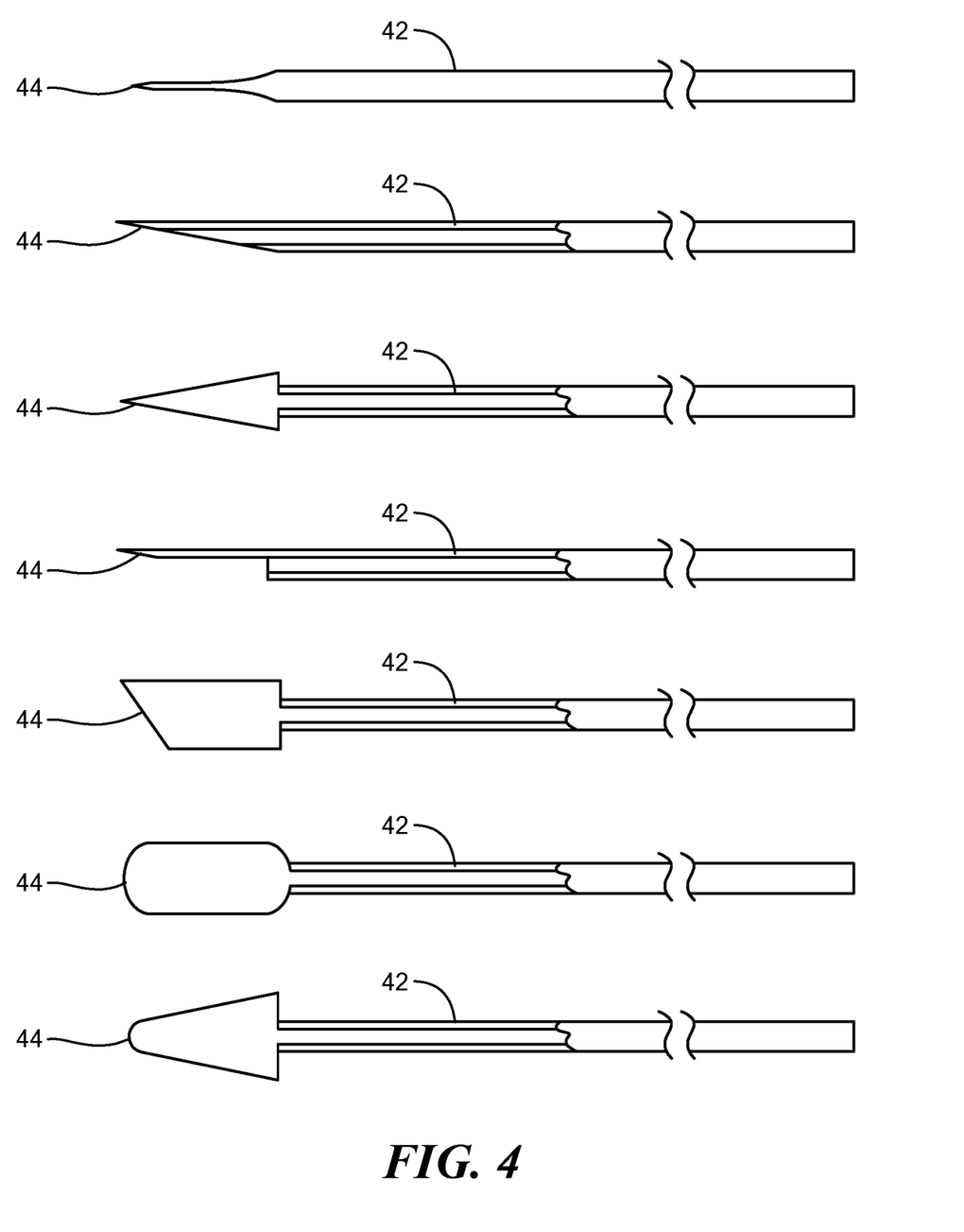
FIG. 4 are top views of exemplary active electrodes for the electrosurgical hand piece shown in FIG. 1.

Referring now to FIGS. 2-3, a tip 44 of active electrode 42 may define any number of shapes and sizes depending on the application. For example, for microsurgery in the brain, the tip 44 may define a tapered tip, for example, in the shape of an arrow or needle such that current density is maximized to generate thermal energy sufficient to cut tissue. In one configuration, the entirety or at least substantially the entirety of the tip 44 is coated with an insulator such that only a portion of the tip 44 is exposed, while in other configurations the tip 44 is uncoated. In the coated a configuration, the current density at the exposed portion of the tip 44 may be high enough to generate plasma mediated reactions to cut through tissue. In other configurations, for example those shown in FIG. 4, the tip 44 may be other shapes, for example, a wire shape, paddle shape, circular, or have a rounded distal end. The tip 44 may further be flat and/define at least one planar surface. In other configurations, while active electrode 42 may define a hypotube for transporting fluids such as saline, the tip 44 may be solid such that a fluid port (not shown) may be defined by the active electrode 42 between the tubular portion of the active electrode 42 and the tip 44.

Continuing to refer to FIGS. 2-3, the shaft 30, which is coupled to the first conductor 37, may function as the opposite pole in a bipolar arrangement with the active electrode 42 for the current pathway. For example, the shaft 30 may define a flexible tissue contact element that extends distally from the distal end 34 of the shaft 30 to define a return electrode 46. For example, the shaft 30 may define a thin piece of elastic conductor, for example, stainless steel, or Nitinol, that is atraumatic to the tissue surface. As shown in FIGS. 2-3, the return electrode 46 may be curvilinear in shape, or any shape, and may be biased in a curved configuration away from the active electrode 42 such that the distal end of the return electrode 46 is in contact with a tissue surface when in use. In one configuration, the return electrode 46 is flexible, bendable, and may be independently advanceable and retractable to provide for contact with the target tissue. For example, the return electrode 46 may be a separate component from the shaft 30, but be in electrical communication with the shaft such that it is grounded, that may be movable and/or torqueable with respect to the shaft by one or more pull wires or other actuators (not shown).

The return electrode 46 may define a larger surface area than that the active electrode 42 such that energy transferred from the active electrode 42 is diffused by the larger surface area on the return electrode 46. This provides for precise cutting or coagulation of tissue while minimizing collateral damage to surrounding tissue. In one configuration, the return electrode 46 and elongated shaft is uncoated and in another configuration the return electrode 46 elongate shaft 30 is substantially entirely coated with an insulator such that the tip of the return electrode is exposed and in contact with the tissue.

Continuing refer to FIGS. 2 and 3, disposed within the lumen 36 of the shaft 30 is an alignment element 48 configured to maintain the position of the active electrode 42 with respect to the shaft 30. The alignment element 48 may be insulated and disposed at the proximal end 32 or distal end 34 of the shaft 30. In one configuration, the alignment element 48 defines a slot or lumen sized to receive and retain the active electrode 42 and/or the fluid conduit 38. In such a configuration, the active electrode 42 may be prevented from moving longitudinally or radially such that when the user performs microsurgery the active electrode 42 is stabilized.

Figure 5:
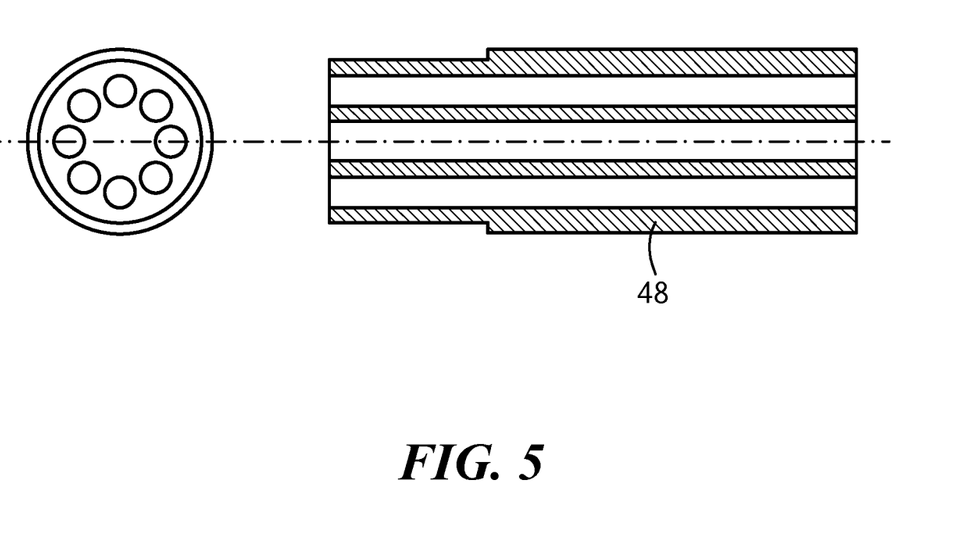
FIG. 5 is another configuration for the alignment element shown in FIG. 3.

Referring now to FIG. 5, in one configuration, fluid conduit 38 and/or the lumen 36 may be configured for use as a smoke evacuation channel. In such a configuration, the alignment element 48 may be modified by providing channels through it to provide passage from distal end 34 to proximal end and then via tubing to the vacuum port or pump.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings without departing from the scope of the following claims.

What is claimed is:

1. An electrosurgical medical device, comprising:
   an elongate shaft defining a proximal end, a distal end, and a lumen there through;
   a fluid conduit disposed within the lumen;
   a first electrode at least partially disposed within the lumen and extending distally from the distal end of the shaft, the first electrode being sized and configured to cut tissue with radiofrequency energy;
   a curvilinear second electrode arranged in a bipolar configuration with the first electrode and extending away from the first electrode, the second electrode being coupled to ground and configured to receive radiofrequency energy from the first electrode, the second electrode being continuous with and formed by at least a portion the shaft and extending a distance away from the distal end of the shaft.

2. The device of claim 1, wherein the first electrode defines the fluid conduit.

3. The device of claim 1, wherein the first electrode defines a sharp distal end.

4. The device of claim 1, wherein the second electrode is atraumatic and flexible.

5. The device of claim 1, wherein the surface area of the second electrode is larger than the surface area of the first electrode.

6. The device of claim 1, wherein the first electrode is at least substantially entirely coated with an insulating material.

7. The device of claim 6, wherein the first electrode is a hypotube with a sharp distal end.

8. The device of claim 7, wherein the second electrode is biased in a position away from the shaft.

9. An electrosurgical medical device, comprising:
- an elongate shaft defining a proximal end, a distal end, and a lumen there through;
- a fluid conduit disposed within the lumen;
- a first electrode at least partially disposed within the lumen and extending distally from the distal end of fluid conduit, the first electrode being sized and configured to cut tissue with radiofrequency energy;
- a curvilinear second electrode arranged in a bipolar configuration with the first electrode and extending away from the first electrode, the second electrode being coupled to ground and configured to receive radiofrequency energy from the first electrode, the second electrode being continuous with and formed by at least a portion the shaft and extending a distance away from the distal end of the shaft; and
- an alignment element disposed within the lumen of the shaft, the alignment element configured to maintain the position of the first electrode within the shaft.

10. The device of claim 9, wherein the alignment element defines a lumen therein, and wherein the fluid conduit is received within the lumen of the alignment element.

11. The device of claim 9, wherein the fluid conduit is in fluid communication with a vacuum source and configured to suction smoke.

12. The device of claim 9, wherein the fluid conduit is in fluid communication with a fluid source and configured to provide irrigation.

13. The device of claim 9, wherein the alignment element includes a plurality of lumens configured to transport fluid to and from the proximal end and the distal end of the elongate shaft.

14. The device of claim 9, wherein the first electrode and the second electrode are configured to coagulate tissue with saline dispersed from the fluid conduit.

15. The device of claim 9, wherein the first electrode defines a sharp distal end.

16. The device of claim 9, wherein the second electrode is atraumatic and flexible.

17. The device of claim 9, wherein the surface area of the second electrode is larger than the surface area of the first electrode.

18. An electrosurgical medical device, comprising:
- an elongate shaft defining a proximal end, a distal end, and a lumen there through;
- a fluid conduit disposed within the lumen;
- a first electrode at least partially disposed within the fluid conduit and extending distally from the distal end of fluid conduit, the first electrode being sized and configured to cut tissue with radiofrequency energy, the first electrode defining a tubular portion sized to be received within the fluid conduit;
- a second electrode arranged in a bipolar configuration with the first electrode, the second electrode being coupled to ground and configured to receive radiofrequency energy from the first electrode, the second electrode being continuous with and formed by at least a portion the shaft and extending a distance away from the distal end of the shaft, a surface area of the second electrode being larger than a surface area of the first electrode, the second electrode defining a curvilinear shape and being flexible; and
- an alignment element disposed within the lumen of the shaft, the alignment element configured to maintain the position of the first electrode within the shaft.

* * * * *